United States Patent [19]

Hentze

[11] 4,149,401
[45] Apr. 17, 1979

[54] FURNACE FOR DIFFERENTIAL THERMAL ANALYSIS

[75] Inventor: Günter Hentze, Odenthal-Hahnenberg, Fed. Rep. of Germany

[73] Assignee: Bayer Aktiengesellschaft, Leverkusen, Fed. Rep. of Germany

[21] Appl. No.: 869,887

[22] Filed: Jan. 16, 1978

[30] Foreign Application Priority Data

Feb. 5, 1977 [DE] Fed. Rep. of Germany ....... 2704872

[51] Int. Cl.² .............................................. G01K 17/04
[52] U.S. Cl. ...................................................... 73/15 B
[58] Field of Search .......................................... 73/15 B

[56] References Cited

U.S. PATENT DOCUMENTS

| 3,208,282 | 9/1965 | Bailly | 73/15 |
| 3,535,913 | 10/1970 | Wist | 73/15 |

*Primary Examiner*—Herbert Goldstein
*Attorney, Agent, or Firm*—Sprung, Felfe, Horn, Lynch & Kramer

[57] ABSTRACT

A furnace which is suitable for carrying out differential thermal analysis of long duration comprises two symmetrical halves having equal heat capacities. Equal sized bores are provided in both halves for a sample container. There are additional bores in the lower half for differential thermoelements. The two halves of the furnace are advantageously provided with filament windings of equal electrical resistance.

5 Claims, 1 Drawing Figure

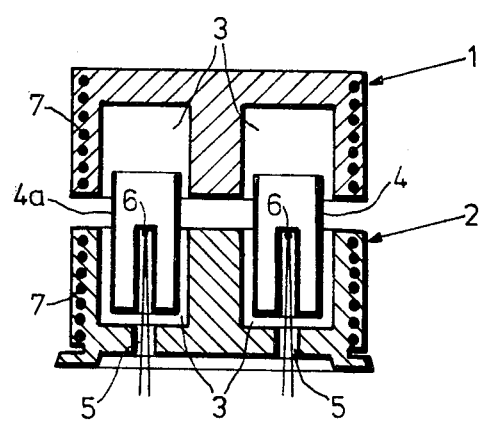

FURNACE FOR DIFFERENTIAL THERMAL ANALYSIS

The invention relates to a furnace for differential thermal analysis of long duration, in which relatively large quantities of samples are examined. Large sample containers are required when carrying out differential thermal analysis with large quantities of samples, for example at very slow heating rates. The large containers naturally require correspondingly large furnaces in which the temperature frequently varies from one location to another.

Relatively large temperature gradients are obtained within the furnace when heating the furnace, particularly in the area of the upper cover of the furnace or the lower seal. These lead to variations in temperature not only in the furnace but also, when using large quantities of samples, within the sample itself. Measurements can be falsified in this way.

The object of the invention is accordingly to provide a furnace in which the temperature is as spatially uniform as possible, for carrying out differential thermal analysis of long duration, in other words for examining large volumes of samples.

According to the invention there is provided a furnace for differential thermal analysis of long duration, which comprises two symmetrical halves having equal heat capacities, in which equal sized bores are provided for receiving a sample container, and additional bores are provided in the lower half for a differential thermoelement. The two halves of the furnace are advantageously provided with filament windings which have the same electrical resistance.

In a furnace of this type, a highly uniform distribution of the temperature may be obtained. This enables very precise differential thermal analyses to be carried out at extremely low heating rates down to $10^{-2}$° C. min$^{-1}$.

An embodiment of the invention is described in more detail below with reference to the accompanying drawing, which is a cross-section through a differential thermal analysis furnace having two symmetrical halves, an upper half 1 and a lower half 2. The halves are formed with symmetrical cylindrical parts. Two large bores 3 are provided symmetrically with respect to each other in the two halves for receiving a sample container 4 and a container 4a for a comparison material, and smaller bores 5 having the same diameter are provided in the lower section 2 for receiving differential thermoelements 6 and optionally control elements. The sample container 4 may have a volume of, for example, about 20 cm$^3$.

Both halves of the furnace 1 and 2 are provided with filament windings 7 in their external jackets so that the same heating power is generated when a given voltage is applied in each half of the furnace. The heating rate is adjusted in such a way that the temperature in the comparison material rises linearly with time. The comparison material must not undergo a thermal reaction in the temperature range being used for the test. If the difference between the temperature of the sample and the temperature of the comparison material is plotted as a function of temperature, the desired differential thermal analysis diagram is obtained.

What we claim is:

1. A furnace for long term differential thermal analysis comprising: two symmetrical upper and lower halves having equal heat capacities, each half having two bores, each aligned with a corresponding one in the other half and all of equal size, wherein each set of two aligned bores is provided for receiving a sample container, and additional bores are provided in the lower half for a differential thermoelement.

2. A furnace according to claim 1, wherein the two halves of the furnace have filament windings of equal electrical resistance.

3. A furnace according to claim 2, wherein the filament windings are disposed in the outer peripheral portion of the furnace halves.

4. A furnace according to claim 2, wherein the halves are cylindrical and the filament windings are disposed around the circumferential portion.

5. A furnace according to claim 1, wherein each additional bore is dispersed concentrically with and below one bore in the lower half and has a smaller diameter.

* * * * *

UNITED STATES PATENT AND TRADEMARK OFFICE
CERTIFICATE OF CORRECTION

PATENT NO. : 4,149,401
DATED : April 17, 1979
INVENTOR(S) : GUNTER HENTZE, et al It is certified that error appears in the above—identified patent and that said Letters Patent are hereby corrected as shown below:

Title Page, after "References Cited" please add:

--OTHER PUBLICATIONS

Muller "Differential Thermal Analysis" in Analytical Chemistry Vol. 35 #4 4/63.

Jong "Verification of Use of Peak Area for Quantitutive Differential Thermal Analysis" in J. of Am. Ceramic Soc. Vol. 40 #2 2/59 page 42-49.--

Signed and Sealed this

Ninth Day of October 1979

[SEAL]

Attest:

RUTH C. MASON
*Attesting Officer*

LUTRELLE F. PARKER
*Acting Commissioner of Patents and Trademarks*